United States Patent [19]

Petrillo, Jr.

[11] 4,384,123

[45] May 17, 1983

[54] PHOSPHINYLALKANOYL SUBSTITUTED PROLINES

[75] Inventor: Edward W. Petrillo, Jr., Pennington, N.J.

[73] Assignee: E. R. Squibb & Sons, Inc., Princeton, N.J.

[21] Appl. No.: 326,082

[22] Filed: Nov. 30, 1981

Related U.S. Application Data

[62] Division of Ser. No. 212,911, Dec. 4, 1980, Pat. No. 4,337,201.

[51] Int. Cl.$^3$ ............................................. C07D 207/12
[52] U.S. Cl. ...................................... 548/409; 548/413
[58] Field of Search ............ 260/326.2, 326.36, 326.35, 260/326.47, 326.42, 326.46; 548/409, 413

[56] References Cited

U.S. PATENT DOCUMENTS

| | | | |
|---|---|---|---|
| 4,105,776 | 8/1978 | Ondetti et al. | 424/274 |
| 4,154,935 | 5/1979 | Ondetti et al. | 260/326.2 |
| 4,168,267 | 9/1979 | Petrillo, Jr. | 260/326.2 |
| 4,181,663 | 1/1980 | Haugwitz | 260/326.46 |
| 4,217,359 | 8/1980 | Krapcho | 260/326.46 |
| 4,234,489 | 11/1980 | Ondetti et al. | 260/326.25 |
| 4,288,368 | 9/1981 | Haugwitz | 260/326.35 |
| 4,296,033 | 10/1981 | Petrillo, Jr. | 260/326.2 |
| 4,307,110 | 12/1981 | Condon et al. | 260/326.2 |
| 4,310,461 | 1/1982 | Krapcho et al. | 260/326.2 |
| 4,311,697 | 1/1982 | Krapcho | 260/326.42 |
| 4,311,705 | 1/1982 | Ondetti et al. | 260/326.36 |
| 4,316,906 | 2/1982 | Ondetti et al. | 260/326.2 |

FOREIGN PATENT DOCUMENTS

| | | | |
|---|---|---|---|
| 9183 | 4/1980 | European Pat. Off. | |
| 2027025 | 2/1980 | United Kingdom | 260/326.2 |
| 2028327 | 3/1980 | United Kingdom | 260/326.2 |

*Primary Examiner*—Jane T. Fan
*Attorney, Agent, or Firm*—Lawrence S. Levinson; Donald J. Barrack

[57] ABSTRACT

Esters of phosphinylalkanoyl prolines and phosphinylalkanoyl substituted prolines are inhibitors of angiotensin converting enzyme and are useful in the treatment of hypertension.

8 Claims, No Drawings

PHOSPHINYLALKANOYL SUBSTITUTED PROLINES

This is a division of application Ser. No. 212,911 filed Dec. 4, 1980 now U.S. Pat. No. 4,337,201, issued June 29, 1982.

BACKGROUND OF THE INVENTION

The recent literature discloses a variety of mercaptoacyl amino acids which are useful for inhibiting the conversion of angiotensin I to angiotensin II in mammals, and are, therefore, useful in the treatment of hypertension.

U.S. Pat. No. 4,105,776, issued Aug. 8, 1978 discloses mercaptoacyl amino acids wherein the amino acid is, inter alia, proline, 4-hydroxyproline and 4-alkylproline.

U.S. Pat. No. 4,154,935, issued May 15, 1979 discloses mercaptoacyl amino acids wherein the amino acid is, inter alia, 4-halogen substituted proline or 4,4-dehalogen substituted proline.

United Kingdom patent application No. 2,027,025, published Feb. 13, 1980, discloses mercaptoacyl amino acids wherein the amino acid is 5-substituted prolines.

United Kingdom patent application No. 2,028,327, published Mar. 5, 1980, discloses mercaptoacyl amino acids wherein the amino acid is, inter alia, proline substituted in the 3- or 4-position with a group having the formula R—S— or R—O— wherein R is alkyl, alkenyl, alkynyl, phenyl, substituted phenyl, phenylalkyl or substituted phenylalkyl.

U.S. Pat. No. 4,168,267, issued Sept. 18, 1979 discloses phosphinylalkanoyl prolines and esters or salts thereof.

The compounds disclosed by the above mentioned references are disclosed as inhibitors of the action of angiotensin converting enzyme in mammals and as useful hypotensive agents.

BRIEF DESCRIPTION OF THE INVENTION

Compounds having the formula

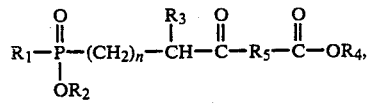

and salts thereof, have hypotensive activity, In formula I, and throughout the specification, the symbols are as defined below.

$R_1$ is alkyl, aryl, arylalkyl, cycloalkyl, or cycloalkyl(alkyl);

$R_2$ and $R_4$ each is independently hydrogen, alkyl, arylalkyl, or

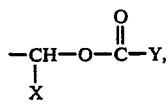

wherein X is hydrogen, alkyl, or phenyl and Y is hydrogen, alkyl, phenyl or alkoxy, or together X and Y are

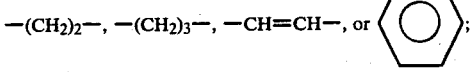

$R_3$ is hydrogen or alkyl;
—$R_5$—$COOR_4$ is

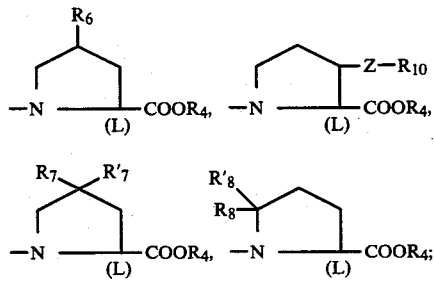

$R_6$ is hydrogen, hydroxy, alkyl, halogen, azido, amino, cycloalkyl, aryl, arylalkyl, carbamoyloxy

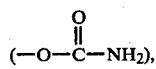

N,N-dialkylcarbamoyloxy, or —Z—$R_9$;

$R_7$ and $R_7'$ are the same and each is halogen or —Z—$R_{10}$, or $R_7$ and $R_7'$ together are =O, —O—(CH$_2$)$_m$—O— or —S—(CH$_2$)$_m$—S—;

$R_8$ is hydrogen and $R_8'$ is phenyl, 2-hydroxyphenyl or 4-hydroxyphenyl or $R_8$ and $R_8'$ together are =O;

$R_9$ is alkyl, aryl, arylalkyl, 1- or 2-naphthyl, or biphenyl;

$R_{10}$ is alkyl, aryl or arylalkyl;

Z is oxygen or sulfur;

n is 0 or 1; and m is 1 or 2; with the proviso that if —$R_5$—$COOR_4$ is

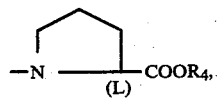

at least one of $R_2$ and $R_4$ is

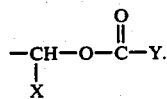

The term "aryl", as used throughout the specification either by itself or as part of a larger group, refers to phenyl or phenyl substituted with halogen, alkyl, alkoxy, alkylthio, hydroxy, alkanoyl, nitro, amino, dialkylamino, or trifluoromethyl groups. Phenyl and monosubstituted phenyl are preferred and phenyl is the most preferred.

The term "alkyl", as used throughout the specification either by itself or as part of a larger group, refers to groups having 1 to 10 carbon atoms. Alkyl groups having 1 to 4 carbon atoms are preferred.

The term "cycloalkyl", as used throughout the specification either by itself or as part of a larger group, refers to groups having 3 to 7 carbon atoms.

The term "alkoxy", as used throughout the specification either by itself or as part of a larger group, refers to groups having 1 to 8 carbon atoms. Alkoxy groups having 1 to 3 carbon atoms are preferred.

The term "halogen", as used throughout the specification either by itself or as part of a larger group, refers to fluorine, chlorine, bromine and iodine. The preferred halogen groups are fluorine and chlorine.

The term "alkanoyl", as used throughout the specification either by itself or as part of a larger group, refers to groups having 2 to 9 carbon atoms.

DETAILED DESCRIPTION OF THE INVENTION

The compounds of formula I, and salts thereof, are hypotensive agents. They inhibit the conversion of the decapeptide angiotensin I to angiotensin II and, therefore, are useful in reducing or relieving angiotensin related hypertension. The action of the enzyme renin on angiotensinogen, a pseudoglobulin in blood plasma, produces angiotensin I. Angiotensin I is converted by angiotensin converting enzyme (ACE) to angiotensin II. The latter is an active pressor substance which has been implicated as the causative agent in several forms of hypertension in various mammalian species, e.g., humans. The compounds of this invention intervene in the angiotensinogen→(renin)→angiotensin I→(ACE)-→angiotensin II sequence by inhibiting angiotensin converting enzyme and reducing or eliminating the formation of the pressor substance angiotensin II. Thus by the administration of a composition containing one (or a combination of the compounds of this invention, angiotensin dependent hypertension in a species of mammal (e.g., humans) suffering therefrom is alleviated. A single dose, or preferably two to four divided daily doses, provided on a basis of about 0.1 to 100 mg. per kilogram of body weight per day, preferably about 1 to 15 mg. per kilogram of body weight per day is appropriate to reduce blood pressure. The substance is preferably administered orally, but parenteral routes such as the subcutaneous, intramuscular, intravenous or intraperitoneal routes can also be employed.

The compounds of this invention can also be formulated in combination with a diuretic for the treatment of hypertension. A combination product comprising a compound of this invention and a diuretic can be administered in an effective amount which comprises a total daily dosage of about 30 to 600 mg., preferably about 30 to 330 mg. of a compound of this invention, and about 15 to 300 mg., preferably about 15 to 200 mg. of the diuretic, to a mammalian species in need thereof. Exemplary of the diuretics contemplated for use in combination with a peptide of this invention are the thiazide diuretics, e.g., chlorthiazide, hydrochlorthiazide, flumethiazide, hydroflumethiazide, bendroflumethiazide, methychlothiazide, trichlormethiazide, polythiazide or benzthiazide as well as ethacrynic acid, ticrynafen, chlorthalidone, furosemide, musolimine, bumetanide, triamterene, amiloride and spironolactone and salts of such compounds.

The compounds of formula I can be formulated for use in the reduction of blood pressure in compositions such as tablets, capsules or elixirs for oral administration, or in sterile solutions or suspensions for parenteral administration. About 10 to 500 mg. of a compound of formula I is compounded with a physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the range indicated is obtained.

The phosphinylalkanoyl substituted prolines of formula I can be prepared by reacting a proline derivative have the formula

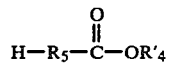

with a phosphinyl-acetic or propionic acid having the formula

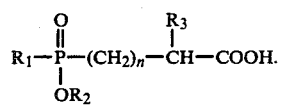

In formula II and throughout the specification, $R_4'$ is alkyl, arylalkyl or

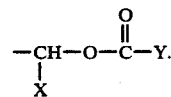

The reaction can be accomplished using known amide bond forming procedures. For example, the reaction can be run in the presence of a coupling agent such as dicyclohexylcarbodiimide, or the acid of formula III can be activated by formation of its mixed anhydride, symmetrical anhydride, acid halide (preferably acid chloride) or acid ester, or by the use of Woodward reagent K, N-ethoxycarbonyl-2-ethoxy-1,2-dihydroquinoline, N,N'-carbonyldiimidazole or the like. A review of these methods can be found in *Methoden der Organischen Chemie* (HoubenWeyl), Vol. XV, part II, page 1 et seq. (1974). The product of the reaction has the formula

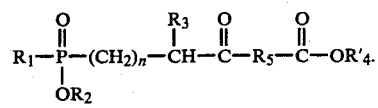

Compounds of formula I wherein $R_2$ is hydrogen can alternatively be obtained by (i) treating a corresponding compound of formula IV wherein $R_2$ is alkyl with a halosilane such as bromotrimethylsilane and then water or (ii) catalytic hydrogenation of a corresponding compound of formula IV wherein $R_2$ is arylalkyl, e.g., using palladium on charcoal. These products have the formula

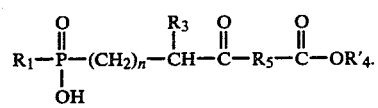

Compounds of formula I wherein $R_4$ is hydrogen, i.e., compounds having the formula

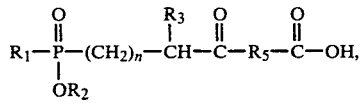

VI can be obtained by basic hydrolysis of a compound of formula IV or V. Alternatively, a compound of formula IV or V wherein $R_4'$ is an easily removable ester group (such as t-butyl) can be treated with trifluoroacetic acid and anisole to obtain the carboxylic acids of formula I.

The phosphinylalkanoyl substituted prolines of formula I wherein n is 1 can alternatively be prepared by reacting a proline derivative of formula II with a phospholane having the formula

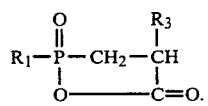

VII

The reaction proceeds most readily when run in the presence of an organic base, e.g., triethylamine, pyridine, N,N-dimethylamine or the like, in an inert organic solvent such as acetonitrile, dichloromethane, ether, tetrahydrofuran, or the like.

Phosphinyl-acetic or propionic acid derivatives of formula III can be prepared using known procedures; see, for example, U.S. Pat. No. 4,168,267, issued Sept. 18, 1979. Phospholanes of formula VII can be prepared following the procedures described in Zh. Obsh. Kim., 37:411 (1967) and Zh. Obsh. Kim., 38:288 (1968).

The proline esters of formula II are known or are readily obtainable using known esterification techniques which are illustrated in the examples. Various substituted prolines are disclosed by Manger et al., Chem. Rev., 66:47 (1966). Ondetti et al. disclose various alkyl, halogen, ether and thioether substituted prolines in U.S. Pat. Nos. 4,105,776, 4,154,935, and U.K. Application No. 2,028,327. Iwao et al. in U.K. Application No. 2,027,025 disclose various 5-substituted prolines.

As disclosed by Krapcho in U.S. Ser. No. 066,119, filed Aug. 12, 1979, the carbamoyloxy substituted prolines can be obtained by reacting the hydroxy substituted N-protected proline with phosgene and then a dialkylamine. Removal of the N-protecting group yields the desired starting material.

As disclosed by Krapcho in U.S. Ser. No. 099,164, filed Nov. 30, 1979, the prolines of the formula

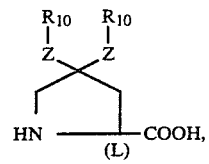

VIII and esters thereof, can be prepared by reacting a keto compound of the formula

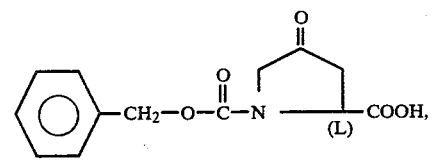

IX or ester thereof, with an alcohol or thiol having the formula $R_{10}$—Z—H  X in the presence of an orthoformate or thioformate of the formula $HC(Z—R_{10})_3$ and an acid such as concentrated sulfuric acid or p-toluenesulfonic acid. Removal of the carbobenzyloxy group by catalytic hydrogenation when Z is oxygen or by treatment with hydrogen bromide and acetic acid when Z is sulfur yields the desired compound.

As disclosed by Krapcho in U.S. Ser. No. 164,985, filed Aug. 7, 1980, the 4-substituted proline starting materials wherein the substituent $R_4$ is cycloalkyl, aryl, or arylalkyl can be prepared by reacting a 4-keto proline of formula IX, or ester thereof, with a solution of Grignard reagent $R_6$—Mg—halo  X or lithium reagent $R_6$—Li  XII to yield a compound of the formula

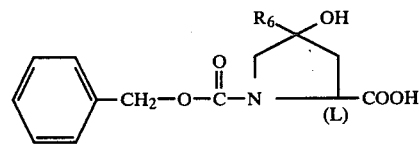

XIII or ester thereof. This compound can be treated with a dehydrating agent such as p-toluenesulfonic acid, sulfuric acid, potassium bisulfate, or trifluoroacetic acid to yield a 3,4-dehydro-4-substituted proline having the formula

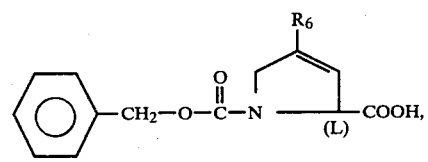

XIV or ester thereof. Removal of the N-benzyloxycarbonyl protecting group and hydrogenation of the resulting compound yields the desired 4-substituted proline derivatives. The substituted proline wherein $R_6$ is cyclohexyl can also be prepared by further hydrogenation of the 4-phenylproline compound.

Additional processes for preparing the compounds of this invention will be apparent to the practitioner of this invention. For example, the carboxyl group of a proline derivative having the formula

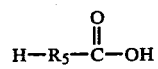

XV can be protected, e.g., by conversion to an amine salt, or a 2-hydroxyethyl or diphenylmethyl ester, reacted with a phosphinyl-acetic or propionic acid of formula III, and then deprotected to yield a product of formula VI.

Esterification of a product of formula VI using art-recognized procedures yields the corresponding product of formula IV.

An alternative procedure for preparing the compounds of this invention wherein $R_2$ is alkyl, arylalkyl or

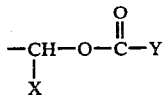

and $R_4$ is hydrogen comprises first alkylating the corresponding compound of formula V and then subjecting the resulting compound to basic hydrolysis.

The practitioner of this invention will also appreciate that the phosphinylalkanoyl-4-aminoprolines of this invention can be prepared from the corresponding phosphinylalkanoyl-4-azidoprolines and the phosphinylalkanoyl-4-azidoprolines can be prepared from the corresponding phosphinylalkanoyl-4-hydroxyprolines.

The compounds of this invention wherein one of $R_2$ and $R_4$ is

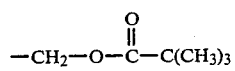

(i.e., pivaloyloxymethyl) and the other is hydrogen are preferred esters of this invention.

The compounds of this invention wherein at least one of $R_2$ or $R_4$ is hydrogen, form basic salts with various inorganic and organic bases which are also within the scope of the invention. Such salts include ammonium salts, alkali metal salts like lithium, sodium and potassium salts (which are preferred), alkaline earth metal salts like the calcium and magnesium salts, salts with organic bases, e.g., dicyclohexylamine salt, benzathine, N-methyl-D-glucamine, hydrabamine salts, salts with amino acids like arginine, lysine and the like. The non-toxic, physiologically acceptable salts are preferred, although other salts are also useful, e.g., in isolating or purifying the product. The salts are formed using conventional techniques.

The following examples are specific embodiments of this invention.

EXAMPLE 1

(S)-7-[[Ethoxy(4-phenylbutyl)phosphinyl]acetyl]-1,4-dithia-7-azaspiro[4.4]nonane-8-carboxylic acid, methyl ester

[Ethoxy(4-phenylbutyl)phosphinyl]acetic acid (2.42 g), acetonitrile (25 ml) and carbonyldiimidazole (1.32 g) are allowed to stir under argon at 0° C. for 1 hour. 4,4-Ethylenedithioproline, methyl ester (1.48 g) is added to the mixture, which is then allowed to stir at room temperature for about 16 hours. The solvent is stripped off leaving an oil that is diluted with ethyl acetate (100 ml), washed with 5% potassium bisulfate, washed with saturated sodium bicarbonate and filtered through anhydrous sodium sulfate. The solvent is stripped off yielding the title compound as an oil (3.44 g).

EXAMPLE 2

(S)-7-[[Hydroxy(4-phenylbutyl)phosphinyl]acetyl]-1,4-dithia-7-azaspiro[4.4]nonane-8-carboxylic acid, methyl ester (S)-7-[[Ethoxy(4-phenylbutyl)phosphinyl]acetyl]-1,4-dithia-7-azaspiro[4.4]nonane-8-carboxylic acid, methyl ester (3.44 g) and dry dichloromethane (15 ml) are added to a flask under an argon atmosphere. Using a gas-tight syringe, bromotrimethylsilane (1.5 ml) is added to the flask, which is stirred for about 16 hours at room temperature. Ethyl acetate (50 ml) and water (10 ml) are added to the flask and stirred for 30 minutes. The mixture is diluted with ether and transferred to a separatory funnel. The organic layer is extracted with saturated sodium bicarbonate (two 25 ml portions) and the extract is acidified to pH 1.0 to precipitate product which is extracted into ethyl acetate. The ethyl acetate extract is washed with brine, run through sodium sulfate to dry, and the solvent is stripped leaving the title compound as an oil (2.99 g).

EXAMPLE 3

(S)-7-[[Hydroxy(4-phenylbutyl)phosphinyl]acetyl]-1,4-dithia-7-azaspiro[4.4]nonane-8-carboxylic acid (S)-7-[[Hydroxy(4-phenylbutyl)phosphinyl]acetyl]-1,4-dithia-7-azaspiro[4.4]nonane-8-carboxylic acid, methyl ester (2.99 g) and 1 N sodium hydroxide (15 ml) is stirred for 30 minutes at room temperature. The reaction mixture is extracted with ether (50 ml) and the aqueous phase is acidified with concentrated hydrochloric acid to pH 1.0. A solid precipitates out of solution along with an oil. This is extracted into ethyl acetate, passed through sodium sulfate, and the solvent is stripped yielding 2.74 of the title compound, melting point 105.5°–107° C.

EXAMPLE 4

(S)-7-[[Hydroxy(4-phenylbutyl)phosphinyl]acetyl]-1,4-dithia-7-azaspiro[4.4]nonone-8-carboxylic acid, dilithium salt (S)-7-[[Hydroxy(4-phenylbutyl)phosphinyl]acetyl]-1,4-dithia-7-azaspiro[4.4]nonane-8-carboxylic acid (2.74 g) in 1 N lithium hydroxide (10.6 ml) is passed through a column of 80 ml of ion-exchange resin (AG50WX8 (Li+)). The fractions containing product was filtered through a millipore filter and most of the solvent is stripped off. The eluate is lyophilized to give 2.53 g of the title compound as a powder. The product contains 2 moles of water and has an optical rotation $[\alpha]_D = -13.2°$ (c=13.5 mg/ml, methanol).

EXAMPLE 5

(S)-4-Hydroxy-1-[[ethoxy(4-phenylbutyl)phosphinyl]acetyl]-L-proline, methyl ester A mixture of [ethoxy(4-phenylbutyl)phosphinyl]acetic acid (1.71 g), acetonitrile and carbonyldiimidazole (0.97 g) is stirred under argon at 0° C. for 1 hour. (S)-4-hydroxyproline, methyl ester (0.006 mole) is suspended in acetonitrile, added to the mixture and stirred at room temperature 90 minutes. Solvent is stripped off, and the resulting oil is taken up in ethyl acetate, washed with 5% potassium bisulfate, washed with saturated sodium bicarbonate, washed with brine, dried over magnesium sulfate, and the solvent stripped to leave 2.23 g of the title compound as an oil.

EXAMPLE 6

(S)-4-Azido-1-[[ethoxy(4-phenylbutyl)phosphinyl]acetyl]-L-proline, methyl ester (S)-4-Hydroxy-1-[[ethoxy(4-phenylbutyl)phosphinyl]-L-proline, methyl ester (2.0 g), triphenylphosphine (2.57 g), 2.1 N hydrazoic acid/benzene (12 ml, >5 equivalents) and dry acetonitrile are stirred under argon at room temperature for 30 minutes. Diethylazocarboxylate (1.71 g) in acetonitrile (5 ml) is added dropwise over 30 minutes. After 18 hours the reaction is still incomplete (as shown by thin-layer chromatography) and triphenylphosphine (1 equivalent), diethylazocarboxylate (1 equivalent) and 2.1 N hydrazoic acid (6 ml) are added. After 4 hours the reaction is complete. Nitrogen is bubbled through the solution to remove excess hydrazoic acid and the solvent is stripped leaving an oil. The oil is chromatographed on 100 mg of silica gel, eluting first with ethyl acetate and then with 3% methanol/ethyl acetate to give 1.64 g of the title compound.

EXAMPLE 7

(S)-4-Azido-1-[[hydroxy(4-phenylbutyl)phosphinyl]acetyl]-L-proline, methyl ester (S)-4-Azido-1-[[ethoxy(4-phenylbutyl)phosphinyl]acetyl]-L-proline, methyl ester (1.60 g), dry dichloromethane and bromotrimethylsilane (0.85 g) are stirred under argon at room temperature. After 19 hours, an additional equivalent of bromotrimethylsilane is added and stirring is continued for 2 hours. Excess bromotrimethylsilane and dichloromethane is removed in vacuo and the residue is treated with ethyl acetate/water and stirred for 15 minutes. The layers are separated and the ethyl acetate layer is extracted with saturated sodium bicarbonate. The aqueous extracts are acidified to pH 1.0 with concentrated hydrochloric acid and extracted with ethyl acetate. The extract is washed with water, brine, dried over sodium sulfate, and the solvent stripped to yield 1.35 g of the title compound as an oil.

EXAMPLE 8

(S)-4-Azido-1-[[hydroxy(4-phenylbutyl)phosphinyl]acetyl]-L-proline (S)-4-Azido-1-[[hydroxy(4-phenylbutyl)phosphinyl]acetyl]-L-proline, methyl ester (1.30 g) and 1 N sodium hydroxide (about 15 ml) is stirred for 30 minutes. The reaction mixture is acidified with concentrated hydrochloric acid, extracted with ethyl acetate, washed with water, washed with brine, dried over sodium sulfate, and the solvent is stripped yielding 1.11 g of the title compound having an optical rotation $[\alpha]_D = -22.3°$ (c=10 mg/ml, methanol). The product contains ½ mole of water.

EXAMPLE 9

(S)-4-Amino-1-[[hydroxy(4-phenylbutyl)phosphinyl]acetyl]-L-proline

A mixture of (S)-4-azido-1-[[hydroxy(4-phenylbutyl)phosphinyl]acetyl]-L-proline (0.8 g) acetic acid (about 20 ml) and 10% palladium on charcoal is hydrogenated on a Parr apparatus for 3 hours. The reaction mixture is filtered through Celite to remove the catalyst and the solvent is stripped leaving an oil. The oil is diluted with water and washed several times with ethyl acetate. The aqueous phase is lyophilized yielding 0.48 g of crude product as a solid. Crude product (400 mg) is run on a column of ion-exchange resin AG50X8 (about 30 ml), eluting first with water and then with a pyridine-acetic acid buffer (pH 6.5). The fractions containing the desired material are combined and evaporated leaving a glass, which is dissolved in water and lyophilized yielding 300 mg of the title compound having an optical rotation $[\alpha]_D = -24.8°$ (c=10 mg/ml, methanol).

EXAMPLE 10

(R)-1-[[Ethoxy(2-phenylethyl)phosphinyl]acetyl-4-hydroxy-L-proline]methyl ester

[Ethoxy(2-phenylethyl)phosphinyl]acetic acid (1.27 g) and carbonyldiimidazole (0.8 g) are stirred in 25 ml of acetonitrile at 0° C. for 1 hour. trans-4-Hydroxy-L-proline, methyl ester hydrochloride (1.0 g) is shaken with triethylamine (0.76 ml) in 10 ml of acetonitrile and filtered directly into the reaction mixture. After standing under nitrogen for 6 days at room temperature, the mixture is taken up in ethyl acetate (500 ml) and 5% sodium bisulfate (10 ml). The organic layer is washed with brine (10 ml), followed by saturated sodium bicarbonate, a second brine washing, and then dried over sodium sulfate and evaporated. The residue, 1.8 g, is crystallized from toluene yielding 0.6 g of the title compound, melting point 126°–128° C.

EXAMPLE 11

(S)-7-[[Hydroxy(2-phenylethyl)phosphinyl]acetyl]-1,4-dioxa-7-azaspiro[4.4]nonane-8-carboxylic acid, ammonia salt (A)

(S)-7-[[Benzyloxy(2-phenylethyl)phosphinyl]acetyl]-1,4-dioxa-7-azaspiro[4.4]nonane-8-carboxylic acid, 2-hydroxyethyl ester Carbonyldiimidazole (2.04 g) is added to a cooled solution (0° C.) of benzyloxy(2-phenylethyl)phosphinylacetic acid (4.0 g) in acetonitrile (50 ml) and the mixture is stirred for 1 hour. A solution of 1,4-dioxa-7-azaspiro[4.4]nonane-8-carboxylic acid, 2-hydroxyethyl ester is added and stirred for 1 hour at 0° C. and for about 16 hours at room temperature. The mixture is taken up in ether, washed with 5% potassium busulfate, followed by brine, saturated sodium bicarbonate and two additional brine washes, and then dried over sodium sulfate and evaporated to give 5.6 g of an oil. The oil is flash chromatographed on silica gel eluted with ethyl acetate and ethyl acetate/methanol (9:1) yielding 3.5 g of the title compound as an oil.

(B)

(S)-7-[[Hydroxy(2-phenylethyl)phosphinyl]acetyl]-1,4-dioxa-7-azaspiro[4.4]nonane-8-carboxylic acid, ammonia salt (S)-7-[[Benzyloxy(2-phenylethyl)phosphinyl]acetyl]-1,4-dioxa-7-azaspiro[4.4]nonane-8-carboxylic acid, 2-hydroxyethyl ester (3.3 g) is dissolved in 50 ml of methanol, and lithium hydroxide monohydrate (0.54 g) dissolved in a small amount of water is added. The mixture is stirred for 1 hour at room temperature and hydrogenated over 1 g of 10% palladium on charcoal at 1 atmosphere for 3 hours. The mixture is stirred for 1 hour at room temperature and hydrogenated over 1 g of 10% palladium on charcoal at 1 atmosphere for 3 hours. The mixture is filtered through Celite, the filtrate evaporated to dryness and the residue dissolved in water which is filtered through a Millipore filter and lyophilized yielding 2.84 g of material. Chromatography of this material on 150 ml of Sephadex (OH form, pH 7.4) eluted with a gradient buffer (0.005 M to 0.5 M ammonium bicarbonate). Fractions which are pure (electrophoresis) are combined, evaporated and lyophilized from water (twice) yielding 1.1 g of the title compound having an optical rotation $[\alpha]_D = -25.9°$ (c=1, water).

EXAMPLE 12

1-[[Hydroxy(4-phenylbutyl)phosphinyl]acetyl]-L-proline, (2,2-dimethyl-1-oxopropoxy)methyl ester Hydroxy(4-phenylbutyl)phosphinyl acetic acid (51.2 g) is suspended in 300 ml of dichloromethane and 1 ml of dimethylformamide in a magnetically-stirred 1000 ml three-neck flask with thermometer and condenser. The mixture is cooled to 5° C. with an ice bath and thionyl chloride (16.1 ml) is added. The bath is removed and the mixture is stirred at room temperature for forty-five minutes. A heating mantle is fitted and the mixture is refluxed for seventy-five minutes. Steady evolution of gas continues until the end of the reflux period, when it stops. The flask is cooled to 5° C. and a solution of proline pivaloyloxymethyl ester tosylate (86.0 g) in 300 ml of dichloromethane (previously dried with 10 g of molecular sieves) is added. Triethylamine (85 ml) is added, causing a rise in temperature to 25° C. The mixture is stirred for about 16 hours and then washed with three 100 ml portions of 1 N HCl, then brine, and evaporated to a residue (106.6 g). The residue is dissolved in 400 ml of acetone and added dropwise through a needle to 2000 ml of water containing seed crystal and vigorously stirred in a 5000 ml flask. The product precipitates as a powder which is filtered immediately and dried at first in vacuo (1 mm, dry ice trap), then over silica gel to yield 86.5 g of the title compound, melting point 63°–66° C.

Anal. Calc'd. for $C_{23}H_{35}NO_7P\cdot H_2O$: C, 56.90; H, 7.47; N, 2.89; P, 6.38; Found: C, 57.02; H, 7.35; N, 2.94; P, 6.4.

EXAMPLE 13

(S)-7-[[(Ethoxy(4-phenylbutyl)phosphinyl]acetyl]-1,4-dithia-7-azaspiro[4.4]nonane-8-carboxylic acid, (2,2-dimethyl-1-oxopropoxy)methyl ester (A)

(S)-7-[(1,1-Dimethylethoxy)carbonyl]-1,4-dithia-7-azaspiro[4.4]nonane-8-carboxylic acid, (2,2-dimethyl-1-oxopropoxy)methyl ester To a mixture of 7.0 g of 1,4-dithia-7-azaspiro[4.4]nonane-8-carboxylic acid, hydrochloride, 17.4 ml of water and 12.1 ml of triethylamine under argon at room temperature is added a solution of 7.8 g of 2-(t-butoxycarbonyloxyimino)-2-phenylacetonitrile in 17.4 ml of dioxane. After 3 hours the reaction mixture is diluted with water and washed twice with ether. The aqueous portion is acidified with concentrated hydrochloric acid and the resulting oil is extracted into ethyl acetate. The ethyl acetate layer is washed with water and brine, dried over magnesium sulfate, and the solvent is stripped yielding an oil. The oil crystallizes on standing yielding 8.9 g of material.

The above material is dissolved in dimethylformamide, treated with (3.7 g) and chloromethyl pivalate (5.2 ml) and the resulting mixture is stirred at room temperature for 16 hours under argon. The reaction mixture is partitioned between water and ethyl acetate, and the organic phase is washed with saturated sodium bicarbonate, water, brine and dried (MgSO4). The solvent is stripped to obtain an oil (10.3 g). The crude product is chromatographed on silica (200 g) eluting with hexane/ether (3/1) to give 8.55 g of the title compound as crystalline solid, melting point 79.5°–81° C. The product is triturated with cold ligroin then filtered to obtain the pure product.

Analysis calc'd for $C_{18}H_{19}NO_6S_2$: C, 51.53; H, 6.97 N, 3.34; S, 15.28; Found: C, 51.34; H, 6.90; N, 3.32; S, 14.87.

(B)

(S)-7-[[(Ethoxy(4-phenylbutyl)phosphinyl]-acetyl]-1,4-dithia-7-azaspiro[4.4.]nonane-8-carboxylic acid, (2,2-dimethyl-1-oxopropoxy)methyl ester A mixture of 1.7 g of [ethoxy(4-phenylbutyl)phosphinyl]acetic acid, acetonitrile and 0.96 g of carbonyldiimidazole is stirred under argon at 0° C. for 1 hour. (S)-7-[(1,1-Dimethylethoxy)carbonyl]-1,4-dithia-7-azaspiro[4.4]nonane-8-carboxylic acid, (2,2-dimethyl-1-oxopropoxy)methyl ester (2.5 g) is treated with trifluoroacetic acid (about 2 ml) and stirred at room temperature for 30 minutes. The trifluoroacetic acid is removed in vacuo, the residue taken up in acetonitrile and added dropwise to the above mixture over a 20 minute period at room temperature. After an additional 2.5 hours, the acetonitrile is stripped and the resulting oil is partitioned between ethyl acetate and water. The layers are separated and the organic portion is washed with 5% potassium sulfate, saturated sodium bicarbonate, brine, dried (MgSO4) and evaporated. The residue (3.4 g) is chromatographed on silica (120 g) eluting with ethyl acetate/dichloromethane (1:1) and yielding 2.7 g of the title compound as a glass.

EXAMPLE 14

(S)-7-[[Hydroxy(4-phenylbutyl)phosphinyl]acetyl]-1,4-dithia-7-azaspiro[4.4]nonane-8-carboxylic acid, (2,2-dimethyl-1-oxopropoxy)methyl ester (S)-7-[[(Ethoxy(4-phenylbutyl)phosphinyl]acetyl]-1,4-dithia-7-azaspiro[4.4]nonane-8-carboxylic acid, (2,2-dimethyl-1-oxopropoxy)methyl ester (2.7 g) in dichloromethane (dried over alumina) is treated with bromotrimethylsilane (1.2 ml) via syringe and the reaction mixture is stirred for 16 hours under argon. The solvent and excess bromotrimethylsilane is evaporated in vacuo and the residue is taken up in ethyl acetate and water and stirred for 15 minutes. The layers are separated and the ethyl acetate is washed with 5% potassium sulfate, water, brine dried (MgSO4) and evaporated. The 2.3 g of crude product is chromatographed on silica (75 g) eluting with dichloromethane/methanol/acetic acid (19/0.5/0.5). After stripping solvent 1.9 g of product is left as a glass.

EXAMPLE 15

(S)-7-[[Hydroxy(4-phenylbutyl)phosphinyl]acetyl]-1,4-dithia-7-azaspiro[4.4]nonane-8-carboxylic acid, (2,2-dimethyl-1-oxopropoxy)methyl ester, lithium salt (S)-7-[[Hydroxy(4-phenylbutyl)phosphinyl]-acetyl]-1,4-dithia-7-azaspiro[4.4]nonane-8-carboxylic acid, (2,2-dimethyl-1-oxopropoxy)methyl ester (1.82 g) is dissolved in 75% water/acetone and treated with 0.1208 g of lithium carbonate. Additional water is added and after 15 minutes the solvent is stripped. The resulting gel is dissolved in water and filtered. The filtrate is run through a Millipore filter and lyophilized to obtain 1.54 g of the product as a solid.

Analysis calc'd for $C_{25}H_{35}NO_7S_2P^-Li^+ \cdot 1.5$ mole $H_2O$: C, 50.83; N, 2.37; H, 6.48; S, 10.86; P, 5.2; Found: C, 51.07; N, 2.36; H, 6.19; S, 10.80; P, 5.5.

EXAMPLE 16

1-[[[(2,2-Dimethyl-1-oxopropoxy)methoxy](4-phenylbutyl)phosphinyl]acetyl]-L-proline, benzyl ester Triethylamine (1.9 ml) and chloromethyl pivalate (2.0 ml) are added to a solution of 3.0 g of [[hydroxy(4-phenylbutyl)phosphinyl]acetyl]-L-proline, benzyl ester in dimethylformamide under an argon atmosphere and the resulting mixture is stirred at room temperature for 6 hours. The reaction mixture is diluted with ethyl acetate, washed with water, brine, dried (MgSO4), and evaporated. The crude product (3.7 g) is chromatographed on silica (80 g) eluting with ethyl acetate/dichloromethane to give 2.96 g of the title compound.

EXAMPLE 17

1-[[[(2,2-Dimethyl-1-oxopropoxy)methoxy](4-phenylbutyl)phosphinyl]acetyl]-L-proline To a solution of 2.6 g of 1-[[[2,2-dimethyl-1-oxopropoxy)methoxy](4-phenylbutyl)phosphinyl]acetyl]-L-proline, benzyl ester is added 250 mg of 10% palladium on charcoal and the resulting mixture is shaken in a Parr hydrogenation apparatus for 2.5 hours. The catalyst is filtered through a Celite bed and the methanol is stripped from the filtrate. The crude product (2.0 g) is chromatographed on silica (50 g), eluting with dichloromethane/acetic acid/methanol (19:0.5:0.5). The solvent is stripped and the remaining acetic acid is azeotroped off with toluene to yield 1.91 g of the title compound as a glass.

EXAMPLE 18

1-[[[(2,2-Dimethyl-1-oxopropoxy)methoxy](4-phenylbutyl)phosphinyl]acetyl]-L-proline, lithium salt 1-[[[(2,2-Dimethyl-1-oxopropoxy)methoxy]-(4-phenylbutyl)phosphinyl]acetyl]-L-proline (1.067 g) is dissolved in 50% acetone/water. Lithium carbonate (0.083 g) is added to the stirring solution. After 30 minutes the acetone and water is removed in vacuo to leave a clear oil. The oil is dissolved in water, run through a Millipore filter and lyophilized to yield 1.0 g of a granular solid.

Analysis of $C_{23}H_{33}NO_7P^-Li^+ \cdot 1$ mole $H_2O$: Found: C, 56.28; N, 2.80; H, 7.19; P, 6.2; Calc'd: C, 56.21; N, 2.85; H, 7.18; P, 6.3.

EXAMPLE 19

(S)-1-[[Ethoxy(4-phenylbutyl)phosphinyl]acetyl]-4-(4-fluorophenoxy)-L-proline

[Ethoxy(4-phenylbutyl)phosphinyl]acetic acid (2.53 g) is dissolved in 30 ml of acetonitrile and cooled to 0° C. in an ice-bath. Carbonyldiimidazole (1.58 g) is added under argon and the resulting mixture is stirred for 1 hour at 0° C. A second solution of 4-(4-fluorophenoxy)-L-proline (2.0 g) is prepared in 20 ml of dry acetonitrile, bis-(trimethylsilyl)acetamide (1.81 g) is added and the mixture is stirred under argon for about 1 hour. The second solution is added to the first and the mixture is stirred for about 16 hours at room temperature. Concentration of the mixture in vacuo yields an oily semisolid which is taken up in 200 ml of dichloromethane, washed with 5% potassium bisulfate, saturated sodium bicarbonate, saturated sodium chloride, and the dichloromethane solution dried over anhydrous magnesium sulfate. The material (3.73 g) is flash chromatographed (20% acetic acid-benzene) to yield 1.36 g of the title compound.

EXAMPLE 20

(S)-4-(4-Fluorophenoxy)-1-[[hydroxy(4-phenylbutyl)phosphinyl]acetyl]-L-proline (S)-4-(4-Fluorophenoxy)-1-[[hydroxy(4-phenylbutyl)phosphinyl]acetyl]-L-proline (0.380 g) and dry dichloromethane (10 ml) are added to a flask under an argon atmosphere at room temperature. Then bis-(trimethylsilyl)acetamide (0.157 g) is added and the mixture is allowed to stir for ½ hour. Bromotrimethylsilane (0.112 ml) is added to the mixture which is stirred for about 16 hours at room temperature. A few drops of water are added to the reaction mixture and stirring is continued for an additional ½ hour. The solvent is stripped off in vacuo yielding 0.372 g of solid. This material is taken up in saturated sodium bicarbonate (15 ml) and washed with ether (two 30 ml portions); this is acidified to pH 2.0 with concentrated hydrochloric acid. The mixture is extracted with ethyl acetate (three 25 ml portions). The ethyl acetate extracts are combined and washed with saturated brine (50 ml) followed by drying over anhydrous MgSO4, and the solvent is then removed leaving 0.110 g of the title compound.

EXAMPLE 21

(S)-4-(4-Fluorophenoxy)-1-[[hydroxy(4-phenylbutyl)phosphinyl]acetyl]-L-proline, dilithium salt (S)-4-(4-Fluorophenoxy)-1-[[hydroxy(4-phenylbutyl)phosphinyl]acetyl]-L-proline (0.1 g) in 1.0 N lithium hydroxide (0.37 ml) is passed through a column of 20 ml of ion-exchange resin (Li+). The fractions containing product are passed through a Millipore filter and most of the solvent is stripped off in vacuo. The eluate is lyophilized and then heated for 24 hours under vacuum at 100° C. to yield 0.017 g of the title compound as a dihydrate, melting point >250° C.

Analysis calc'd for $C_{23}H_{25}NFPO_6Li_2 \cdot 2H_2O$: C, 54.02; H, 4.97; N, 2.74; F, 3.72; P, 6.06; Found: C, 53.91; H, 5.06; N, 2.72; F, 3.73; P, 6.30.

EXAMPLE 22

(cis)-1-[[Ethoxy(4-phenylbutyl)phosphinyl]acetyl]-4-(phenylmethyl)-L-proline, (2,2-dimethyl-1-oxopropoxy)methyl ester (A)

(cis)-1-[(1,1-Dimethylethoxy)carbonyl]-4-(phenylmethyl)-L-proline

To a solution of cis-4-benzyl-L-proline hydrochloride (3 g) and triethylamine (5 g) in water (10 ml) is added a solution of 2-(tert-butoxycarbonyloxyimino)-2-phenylacetonitrile (3.5 g) in dioxane (10 ml). The mixture is stirred at ambient temperature for 4 hours. After the addition of water (30 ml), and washing with ether, the mixture is acidified to a pH of 3-4 with 10% citric acid. The oil that separates is extracted into ethyl acetate, washed with brine, and dried (MgSO4). After concentration in vacuo, the residue (3.7 g) solidifies at room temperature, melting point 145°-149° C. dec.

(B)
(cis)-1-[(1,1-Dimethylethoxy)carbonyl]-4-(phenylmethyl)-L-proline, (2,2-dimethyl-1-oxopropoxy)methyl ester To a solution of (cis)-1-[(1,1-dimethylethoxy)carbonyl]-4-(phenylmethyl)-L-proline (3.4 g) in dry dimethylformamide (3.0 ml) is added solid potassium fluoride (1.5 g), followed by chloromethyl pivalate (2.0 g). After stirring for 16 hours at ambient temperature the mixture is diluted with water (100 ml) and extracted with ethyl acetate. The ethyl acetate solution is washed with 5% sodium bicarbonate, water, brine, and dried (MgSO$_4$). The solvent is removed in vacuo to give an oil residue (5 g). The oil is chromatographed on silica gel (120 g) eluting with ether/hexane (1:3) to give the product (4.4 g) as an oil that solidifies on standing, melting point 60°–62° C.

(C)
(cis)-1-[[Ethoxy(4-phenylbutyl)phosphinyl]acetyl]-4-(phenylmethyl)-L-proline, (2,2-dimethyl-1-oxopropoxy)methyl ester A mixture of (cis)-1-[(1,1-dimethylethoxy)-carbonyl]-4-(phenylmethyl)-L-proline, (2,2-dimethyl-1-oxopropoxy)methyl ester (4.0 g) and 10 ml of trifluoroacetic acid is stirred at combined temperature under argon for 45 minutes. The mixture is concentrated in vacuo at ambient temperature and the residue is dissolved in acetonitrile (40 ml). A second solution is prepared of [ethoxy(4-phenylbutyl)phosphinyl]acetic acid (2.7 g) in acetonitrile (20 ml). The solution is cooled to 0° C., treated with carbonyldiimidazole (1.5 g) and stirred for 1 hour. Triethylamine (1.0 g) is added and the cold bath is removed. The first solution is added dropwise to the second and the mixture is stirred at room temperature for 16 hours and concentrated in vacuo. The residue is dissolved in ethyl acetate (200 ml), washed with 5% potassium acid sulfate, saturated sodium bicarbonate, brine, and dried (MgSO$_4$). The solvent is removed in vacuo; the oil residue (5.6 g) is chromatographed on silica gel (200 g), eluting with dichloromethane/acetone (1:1) to give the product, (4.6 g).

EXAMPLE 23
(cis)-1-[[Hydroxy(4-phenylbutyl)phosphinyl]acetyl]-4-(phenylmethyl)-L-proline, (2,2-dimethyl-1-oxo-propoxy)methyl ester To a solution of (cis)-1-[[ethoxy(4-phenylbutyl)phosphinyl]acetyl]-4-(phenylmethyl)-L-proline,(2,2-dimethyl-1-oxopropoxy)methyl ester (4.5 g) in dichloromethane (50 ml) is added bromotrimethylsilane (2 g). The mixture is stirred at ambient temperature for 16 hours. After concentration in vacuo, the residue is treated with water (25 ml) and extracted into dichloromethane (350 ml), washed with brine, and dried (MgSO$_4$). The solvent is removed in vacuo to give a glass-like solid (4.2 g). The residue is chromatographed on silica gel (220 g) eluting with dichloromethane/methanol/acetic acid (19:1:1), to give the product (2.7 g).

EXAMPLE 24
(cis)-1-[[Hydroxy(4-phenylbutyl)phosphinyl]acetyl]-4-(phenylmethyl)-L-proline,(2,2-dimethyl-1-oxopropoxy)methyl ester, lithium salt To a solution of (cis)-1-[[hydroxy(4-phenylbutyl)phosphinyl]acetyl]-4-(phenylmethyl)-L-proline,(2,2-dimethyl-1-oxopropoxy)methyl ester in acetone/water (80 ml) is added solid lithium carbonate (0.0023 mole). The mixture is stirred at ambient temperature; as the solid gradually dissolves, separation of some orange, polymeric material is observed, plus a trace of solid in suspension. The mixture is filtered after 2 hours, and the filtrate is concentrated in vacuo at ambient temperature. The residue is treated with double distilled water (200 ml) and extracted with ether. An emulsion results that is separated with difficulty. The aqueous layer is Millipore filtered and lyophilized to give the title compound (1.0 g).

Anaylsis calc'd for $C_{30}H_{39}NO_7P.Li.3 H_2O$: C, 58.32; H, 6.36; N, 2.26; P, 5.01; Found: C, 58.15; H, 6.38; N, 2.26; P, 4.98.

EXAMPLE 25
1-[[(Ethoxy)octylphosphinyl]acetyl]-L-proline,(2,2-dimethyl-1-oxopropoxy)methyl ester 1-[(1,1-Dimethylethoxy)carbonyl]-L-proline,(2,2-dimethyl-1-oxopropoxy)methyl ester (3.2 g) and p-toluenesulfonic acid monohydrate (1.72 g) in ethyl acetate (about 50 ml) is treated with 10% palladium on charcoal (300 mg) and shaken on a Parr hydrogenation apparatus at 30 psi for 1 hour. The reaction mixture is filtered through a Celite bed and concentrated to a small volume. The residue is diluted with ether and seeded. The resulting white crystals are filtered and washed four times with ether.

A mixture of [(ethoxy)octylphosphinyl]acetic acid (2.2 g), carbonyldiimidazole (1.4 g), and acetonitrile is stirred under argon at 0° C. for 1 hour. The above p-toluenesulfonic acid salt in about 20 ml of acetonitrile is then added dropwise over a 45 minute period at room temperature. After 60 hours the acetonitrile is stripped and the resulting slurry is diluted with ethyl acetate and water. The layers are separated and the ethyl acetate portion is washed with 5% potassium bisulfate, saturated sodium bicarbonate, brine and dried (MgSO$_4$). The solvent is stripped leaving 3.2 g of the title compound as an oil.

EXAMPLE 26
1-[(Hydroxyoctylphosphinyl)acetyl]-L-proline,(2,2-dimethyl-1-oxopropoxy)methyl ester Bromotrimethylsilane (1.5 ml) is added to a flask containing 3.2 g of 1-[(ethoxyoctylphosphinyl)acetyl]-L-proline,(2,2-dimethyl-1-oxopropoxy)methyl ester and dry dichloromethane under argon at room temperature. After 16 hours excess bromotrimethylsilane and solvent are evaporated in vacuo. The resulting oil is diluted with ethyl acetate and water. After stirring for 5 minutes the layers are separated. The ethyl acetate layer is washed with saturated sodium bicarbonate, 5% potassium sulfate, brine and dried (MgSO$_4$). The solvent is stripped leaving 3.0 g of oil. The oil is chromatographed on silica (120 g) eluting with dichloromethane/methanol/acetic acid (8:1:1). The solvent is stripped and the remaining acetic acid is azeotroped with toluene leaving 1.7 g of the title compound as an oil.

EXAMPLE 27
1-[(Hydroxyoctylphosphinyl)acetyl]-L-proline,(2,2-dimethyl-1-oxopropoxy)methyl ester, lithium salt 1-[(Hydroxyoctylphosphinyl)acetyl]-L-proline,(2,2-dimethyl-1-oxopropoxy)methyl ester (1.5848 g) is dissolved in 80% acetone/water and treated with lithium carbonate (0.13 g). The resulting precipitate is filtered off and the acetone and most of the water is stripped. The resulting soapy solution is diluted with water, Millipore filtered and lyophilized to give a hygroscopic solid (1.3 g).

Anal. Calc'd. for $C_{21}H_{37}NO_7PLi \cdot 1.75\ H_2O$: C, 52.50; H, 7.76; N, 2.91; P, 6.4; Found: C, 52.11; H, 7.81; N, 2.66; P, 6.2.

EXAMPLE 28

(cis)-1-[[Ethoxy(4-phenylbutyl)phosphinyl]acetyl]-4-(phenylthio)-L-proline,(2,2-dimethyl-1-oxopropoxy) methyl ester (A)

(cis)-1-[(1,1-Dimethylethoxy)carbonyl]-4-(phenylthio)-L-proline

To a solution of (cis)-4-(phenylthio)-L-proline (5 g) and triethylamine (3.4 g) in water (13 ml), a solution of 2-(t-butoxycarbonyloxyimino) 2-phenylacetonitrile (6.0 g) in dioxane (13 ml) is added. The mixture is stirred at ambient temperature. After one hour, water (50 ml) is added, the mixture is washed with ethyl acetate and acidified to a pH of 3-4 with 10% citric acid. The oil that separates is extracted into ethyl acetate, washed with brine, and dried (MgSO$_4$). The residue is dissolved in saturated sodium bicarbonate (50 ml) plus water (600 ml). The alkaline solution is washed with ether and acidified to a pH of 4 with 10% citric acid. The oil that separates from solution is extracted into ethyl acetate, washed with brine, and dried (MgSO$_4$). The solvent is removed in vacuo to give the product as an oil (5.9 g) that gradually solidifies, melting point 110°-118° C.

(B)

(cis)-1-[(1,1-Dimethylethoxy)carbonyl]-4-(phenylthio)-L-proline,(2,2-dimethyl-1-oxopropoxy) methyl ester Solid potassium fluoride (2.2 g) is added to a solution of (cis)-1-[(1,1-dimethylethoxy)carbonyl]-4-(phenylthio)-L-proline (5.5 g) in dry dimethylformamide (25 ml), followed by the addition of chloromethylpivalate (3.0 g). The mixture is stirred at room temperature for 20 hours. After the addition of water (40 ml), the mixture is extracted with ethyl acetate, washed with saturated sodium bicarbonate, brine, and dried (MgSO$_4$). The solvent is removed in vacuo and the oil residue (8 g) is chromatographed on silica gel (180 g), eluting with ether/hexane (1:2) to give the product (5 g) as an oil, which gradually solidifies to a waxy solid, melting point 83°-85° C.

(C)

(cis)-1-[[Ethoxy(4-phenylbutyl)phosphinyl]-acetyl]-4-(phenylthio)-L-proline,(2,2-dimethyl-1-oxopropoxy)-methyl ester, lithium salt The mixture (A) is prepared by stirring a solution of (cis)-1-[(1,1-dimethylethoxy)carbonyl]4-(phenylthio)-L-proline,(2,2-dimethyl-1-oxopropoxy) methyl ester (4.2 g) in trifluoroacetic acid (10 ml) at ambient temperature. The mixture is concentrated in vacuo at ambient temperature and the residue is dissolved in dry acetonitrile (40 ml). It is added dropwise to the following mixture (B): a solution of [ethoxy(4-phenylbutyl)phosphinyl]acetic acid in acetonitrile (20 ml) is cooled to 0° C. and carbonyldiimidazole (1.6 g) is added; after stirring at 0° C. for one hour, and immediately preceding the addition of (A), triethylamine (1.1 g) is added. Following the addition of (A) the bath is removed and the mixture is stirred at ambient temperature for 20 hours.

After concentration in vacuo, the residue was dissolved in ethyl acetate (200 ml), washed with 5% potassium acid sulfate, saturated sodium bicarbonate, brine, and dried (MgSO$_4$). The solvent is removed in vacuo. The oil residue (5.6 g) is chromatographed on silica gel (200 g) eluting with dichloromethane/acetone (9:1) to give the product as a viscous oil (3.1 g).

EXAMPLE 29

(cis)-1-[[Hydroxy(4-phenylbutyl)phosphinyl]acetyl]-4-(phenylthio)-L-proline,(2,2-dimethyl-1-oxopropoxy) methyl ester To a solution of (cis)-1-[[ethoxy(4-phenylbutyl)phosphinyl]-acetyl]-4-(phenylthio)-L-proline,(2,2-dimethyl-1-oxopropoxy)methyl ester (3 g) in dichloromethane (30 ml) is added bromotrimethylsilane (1.2 g). The mixture is stirred at room temperature for 16 hours. After the addition of water (15 ml), saturated sodium bicarbonate (25 ml) is added, followed by water (500 ml) to effect solution. The aqueous alkaline solution is washed with ether and acidified to a pH of 3 with concentrated hydrochloric acid. The oil that separates from solution is extracted into ethyl acetate, washed with brine, and dried (MgSO$_4$). The solvent is removed in vacuo to give a residue of 2.5 g which is chromatographed on silica gel (120 g) eluting with dichloromethane/methanol/acetic acid (19:1:1) to give the product (1.8 g) as a glass-like solid.

EXAMPLE 30

(cis)-1-[[Hydroxy(4-phenylbutyl)phosphinyl]acetyl]-4-(phenylthio)-L-proline,(2,2-dimethyl-1-oxopropoxy) methyl ester, lithium salt A solution of lithium carbonate (50 ml) is added dropwise to a stirring solution of (cis)-1-[[hydroxy(4-phenylbutyl)phosphinyl]acetyl]-4-(phenylthio)-L-proline,(2,2-dimethyl-1-oxopropoxy) methyl ester (0.5756 g) in acetone (10 ml); as the stirring solution becomes turbid, the turbidity is clarified by the addition of acetone, so that the final volume of the reaction mixture is 120 ml. A trace of orange polymeric material that separates from solution is removed by filtration. The mixture is concentrated to a volume of 50 ml, and is Millipore filtered and lyophilized to give the title compound (0.6 g).

Analysis calc'd for $C_{29}H_{37}NO_7PS \cdot Li \cdot 2.5\ H_2O$: C, 55.57; H, 5.95; N, 2.23; P, 4.94; S, 5.12; Found: C, 55.67; H, 6.06; N, 2.12; P, 4.80; S, 5.38.

EXAMPLE 31

(cis)-1-[[Ethoxy(4-phenylbutyl)phosphinyl]acetyl]-4-methoxy-L-proline,(2,2-dimethyl-1-oxopropoxy) methyl ester (A)

(cis)-1-[(1,1-Dimethylethoxy)carbonyl]-4-methoxy-L-proline,(2,2-dimethyl-1-oxopropoxy) methyl ester Conversion of 5.0 g (cis)-1-[(1,1-dimethylethoxy)carbonyl]-4-methoxy-L-proline, cyclohexylamine salt to the free acid using 50 ml of 10% KHSO$_4$ and extraction into ethyl acetate gives 3.9 g of material. A mixture of the free acid with 2.2 g of chloromethylpivalate and 1.7 g of anhydrous potassium fluoride in 20 ml of dimethylformamide is stirred under argon at room temperature for 16 hours. The solution is diluted with 50 ml of ethyl acetate and treated with 20 ml of water (twice), saturated sodium bicarbonate and brine. The organic fraction is dried and evaporated in vacuo. The residue is triturated with hexane before drying to give 4.3 g of the title compound, melting point 88°–90° C.

(B)

4-Methoxy-L-proline,(2,2-dimethyl-1-oxopropoxy)-methyl ester, tosylate salt

A solution of 3.0 g of (cis)-1-[(1,1-dimethylethoxy)carbonyl]-4-methoxy-L-proline,(2,2-dimethyl-1-oxopropoxy)methyl ester and 1.5 g of p-toluenesulfonic acid in 50 ml of ethyl acetate is treated with 0.3 g of 10% palladium on charcoal and hydrogenated at 30 psi for one hour. The product, which precipitates during this procedure, is dissolved in acetone before filtration. The solvent is evaporated in vacuo to give an oil which gradually solidifies. The material is triturated with ethyl acetate and filtered to give 2.8 g of product, melting point 116°–118° C.

(C)

(cis)-1-[[Ethoxy(4-phenylbutyl)phosphinyl]acetyl]-4-methoxy-L-proline,(2,2-dimethyl-1-oxopropoxy)-methyl ester A stirred solution of 1.9 g of [ethoxy(4-phenylbutyl)phosphinyl]acetic acid in 25 ml of dry acetonitrile is cooled to 0° C. and treated with 1.1 g of carbonyldiimidazole under argon. After 1 hour the solution is treated with 1.04 ml of triethylamine and the ice bath is removed. A second solution is prepared consisting of 2.8 g of 4-methoxy-L-proline,(2,2-dimethyl-1-oxopropoxy)methyl ester, tosylate salt in 25 ml of dry acetonitrile and is added to the first solution. The resulting mixture is stirred at room temperature for 16 hours. After evaporation of the solvent in vacuo, the oil residue is dissolved in ethyl acetate and extracted with 5% potassium sulfate, saturated sodium bicarbonate and brine. The organic layer is dried and evaporated in vacuo to give 2.4 g of crude product. This material is combined with 1.1 g of crude product from another experiment and chromatographed using acetone/ethyl acetate (3:1) to give 2.9 g of product.

Analysis calc'd for $C_{26}H_{40}NPO_8 \cdot H_2O$: C, 57.44; H, 7.72; N, 2.57; Found: C, 57.87; H, 7.49; N, 2.47.

EXAMPLE 32

(cis)-1-[[Hydroxy(4-phenylbutyl)phosphinyl]acetyl]-4-methoxy-L-proline,(2,2-dimethyl-1-oxopropoxy) methyl ester A solution of 2.9 g of (cis)-1-[[ethoxy(4-phenylbutyl)-phosphinyl]acetyl]-4-methoxy-L-proline,(2,2-dimethyl-1-oxopropoxy)methyl ester in 50 ml of dry dichloromethane is treated with 1.0 g of bromotrimethylsilane at 0° C., then stirred at room temperature for 16 hours under argon. The solvent is evaporated in vacuo and the oil residue is dissolved in ether and treated with an excess of saturated sodium. The aqueous portion is treated with 6 N HCl to pH 1.5 and the product is extracted into ethyl acetate, dried and evaporated in vacuo to give 1.4 g of product.

Analysis calc'd for $C_{24}H_{34}NO_8P \cdot \frac{1}{2} H_2O$: C, 57.13; H, 6.99; N, 2.76; Found: C, 56.54; H, 7.98; N, 2.66.

EXAMPLE 33

(cis)-1-[[Hydroxy(4-phenylbutyl)phosphinyl]acetyl]-4-methoxy-L-proline,(2,2-dimethyl-B 1-oxopropoxy) methyl ester, lithium salt A solution of 1.36 g of (cis)-1-[[hydroxy(4-phenylbutyl)phosphinyl]acetyl]-4-methoxy-L-proline,(2,2-dimethyl-1-oxopropoxy)methyl ester is dissolved in 4 ml of dioxane and cooled to 15° C. while adding 27.2 ml of 0.099 N lithium hydroxide. The temperature is reduced to 5° C. during the addition procedure. Lyophilization gives 1.2 g of product, melting point 81°–85° C.

EXAMPLE 34

(trans)-1-[[Ethoxy(4-phenylbutyl)phosphinyl]acetyl]-4-methoxy-L-proline,(2,2-dimethyl-1-oxopropoxy)-methyl ester Following the procedure of Example 31, but starting with (trans)-1-[(1,1-dimethylethoxy)carbonyl]-4-methoxy-L-proline, cyclohexylamine salt, yields the title compound.

Analysis calc'd: $C_{26}H_{40}NO_8P \cdot 1.0\ H_2O$: C, 57.44; H, 7.79; N, 2.57; P, 5.70; Found: C, 57.07; H, 7.37; N, 2.75; P, 5.4.

EXAMPLE 35

(trans)-1-[[Hydroxy(4-phenylbutyl)phosphinyl]acetyl]-4-methoxy-L-proline,(2,2-dimethyl-1-oxopropoxy)-methyl ester Following the procedure of Example 32, but starting with (trans)-1-[[ethoxy(4-phenylbutyl)phosphinyl]acetyl]-4-methoxy-L-proline,(2,2-dimethyl-1-oxopropoxy)methyl ester, yields the title compound.

Analysis calc'd: $C_{24}H_{36}NO_8P \cdot 0.5\ H_2O$: C, 56.90; H, 7.36; N, 2.77; P, 6.12; Found: C, 57.01; H, 7.39; N, 2.72; P, 5.70.

EXAMPLE 36

(trans)-1-[[Hydroxy(4-phenylbutyl)phosphinyl]acetyl]-4-methoxy-L-proline,(2,2-dimethyl-1-oxopropoxy)-methyl ester, lithium salt Following the procedure of Example 33, but starting with (trans)-1-[[hydroxy(4-phenylbutyl)phosphinyl]acetyl]-4-methoxy-L-proline,(2,2-dimethyl-1-oxopropoxy)methyl ester, yields the title compound, $[\alpha]_D = -33.9°$, c = 10 mg/ml methanol.

EXAMPLE 37

(S)-7-[[Ethoxy(4-phenylbutyl)phosphinyl]acetyl]-1,4-dithia-7-azaspiro[4.4]nonane-8-carboxylic acid A mixture of 2.0 g of [ethoxy(4-phenylbutyl)phosphinyl]acetic acid and 1.1 g of carbonyldiimidazole in acetonitrile is stirred under argon at 0° C. for 1 hour and then treated with 1.9 g of triethylamine and 1.7 g of 1,4-dithia-7-azaspiro[4.4]nonane-8-carboxylic acid, hydrochloride. After 4.5 hours the acetonitrile is stripped and the residue is partitioned between ethyl acetate and 1 N HCl. The organic phase is washed with brine, dried (MgSO$_4$), and the solvent is stripped to give 3.2 g of the title compound as an oil.

EXAMPLE 38

(S)-7-[[[(2,2-Dimethyl-1-oxopropoxy)methoxy]-(4-phenylbutyl)phosphinyl]acetyl]-1,4-dithia-7-azaspiro[4.4]nonane-8-carboxylic acid (A)

(S)-7-[[Ethoxy(4-phenylbutyl)phosphinyl]acetyl]-1,4-dithia-7-azaspiro[4.4]nonane-8-carboxylic acid, diphenylmethyl ester (S)-7-[[Ethoxy(4-phenylbutyl)phosphinyl]acetyl]-1,4-dithia-7-aspiro[4.4]nonane-8-carboxylic acid (3.2 g) in ethyl acetate is treated with 2.0 g of diphenyldiazomethane in ethyl acetate. After 3.5 hours, the reaction mixture is partitioned between ethyl acetate and water. The layers are separated and the organic portion is washed with saturated sodium bicarbonate, 5% potassium bisulfate, brine and dried (MgSO$_4$). The solvent is stripped leaving 6.1 g of residue which is chromatographed on 180 g of silica, eluting with ethyl acetate to yield 3.4 g of the title compound as an oil.

(B)

(S)-7-[[Hydroxy(4-phenylbutyl)phosphinyl]acetyl]1,4-dithia-7-azaspiro[4.4]nonane-8carboxylic acid, diphenylmethyl ester (S)-7-[[Ethoxy(4-phenylbutyl)phosphinyl]-acetyl]-1,4-dithia-7-azaspiro[4.4]nonane-8-carboxylic acid, diphenylmethyl ester (3.4 g) in dry dichloromethane is treated with bromotrimethylsilane (1.5 ml) under argon at room temperature. After 3 hours the dichloromethane and excess bromotrimethylsilane are removed in vacuo and the residue taken up in water and ethyl acetate and stirred for 5 minutes. The layers are separated and the organic phase is washed with brine and dried (MgSO$_4$). The solvent is stripped yielding 3.3 g of the title compound as a foam.

(C)

(S)-7-[[[(2,2-Dimethyl-1-oxopropoxy)methoxy]-(4-phenylbutyl)phosphinyl]acetyl]-1,4-dithia-7-azaspiro[4.4]nonane-8-carboxylic acid, diphenylmethyl ester Chloromethylpivalate (1.6 ml) is added to a stirred mixture of (S)-7-[[hydroxy(4-phenylbutyl)phosphinyl]acetyl]-1,4-dithia-7-azaspiro[3.3]nonane-8-carboxylic acid, diphenylmethyl ester (3.3 g), triethylamine (1.5 ml) and dimethylformamide under argon at room temperature. After 16 hours an additional equivalent of triethylamine and chloromethylpivalate is added to the mixture. After an additional 24 hours, the mixture is partitioned between ethyl acetate and water. The layers are separated and the organic phase is washed with saturated sodium bicarbonate, 5% potassium bisulfate, brine and dried (MgSO$_4$). The solvent is stripped leaving 5.0 g of residue which is chromatographed on 150 g of silica gel, eluting with 33% hexane/ethyl acetate to yield 2.4 g of the title compound as an oil.

(D)

(S)-7-[[[(2,2-Dimethyl-1-oxopropoxy)methoxy]-(4-phenylbutyl)phosphinyl]acetyl]-1,4-dithia-7-azaspiro[4.4]nonane-8-carboxylic acid (S)-7-[[[(2,2-Dimethyl-1-oxopropoxy)methoxy]-(4-phenylbutyl)phosphinyl]acetyl]-1,4-dithia-7-azaspiro[4.4]nonane-8-carboxylic acid, diphenylmethyl ester (2.4 g) in dry dichloromethane is treated with 3.0 ml of trifluoroacetic acid under argon at room temperature. After 1 hour, the trifluoroacetic acid and dichloromethane are removed in vacuo and the resulting oil partioned between ethyl acetate and water. The layers are separated and the organic phase is washed with brine, dried (MgSO$_4$) and evaporated. The residue (4.0 g) is chromatographed on 130 g of silica eluting with dichloromethane/acetic acid/methanol (18:1:1) to give (after azeotropic removal of acetic acid with toluene) 1.5 g of the title compound.

EXAMPLE 39

(S)-7-[[[(2,2-Dimethyl-1-oxopropoxy)methoxy]-(4-phenylbutyl)phosphinyl]acetyl]-1,4-dithia-7-azaspiro[4.4]nonane-8-carboxylic acid, lithium salt (S)-7-[[[(2,2-Dimethyl-1-oxopropoxy)methoxy]-(4-phenylbutyl)phosphinyl]acetyl]-1,4-dithia-7-azaspiro[4.4]nonane-8-carboxylic acid (0.48 g) is dissolved in acetone and treated with lithium carbonate (0.0321 g) and water. The solution is stirred for 1.5 hours. The acetone and water are removed in vacuo and the resulting residue is taken up in water, Millipore filtered and lyophilized to give 0.48 g of the title compound.

Analysis for $C_{25}H_{35}NO_7S_2P-Li^+.1.5$ moles $H_2O$:
Calc.: N, 2.37; C, 50.84; H, 6.48; S, 10.86; P, 5.24;
Found: N, 2.42; C, 50.69; H, 6.02; S, 10.28; P, 5.06.

EXAMPLE 40

(trans)-1-[[Hydroxy(4-phenylbutyl)phosphinyl]acetyl]-4-methoxy-L-proline,dilithium salt A solution of 650 mg of (trans)-1-[[hydroxy(4-phenylbutyl)phosphinyl]acetyl]-4-methoxy-L-proline, (2,2-dimethyl-1-oxopropoxy)methyl ester, lithium salt in 15 ml of ethanol and 10 ml of water containing 6 ml of 1 N sodium hydroxide is stirred for 16 hours at room temperature. Ethanol is removed in vacuo and water was added. The aqueous layer is washed with ethyl acetate (discard), acidified with 8 ml of 1 N HCl and extracted twice with ethyl acetate. The organic layer is washed with saturated brine, combined, dried (MgSO$_4$) and concentrated in vacuo. The residue is heated in an oil bath at 75° C. under high vacuum for 2 hours. The residue (500 mg) is dissolved in 1.5 ml of 1 N lithium hydroxide and washed through a column of ion exchange resin (lithium form, 10 ml) with water. The organics containing eluates are combined, Millipore filtered and lyophilized for 16 hours to give 475 mg of product.

EXAMPLE 41

(cis)-1-[[Hydroxy(4-phenylbutyl)phosphinyl]acetyl]-4-methoxy-L-proline,dilithium salt A solution of 200 ml of (cis)-1-[[hydroxy(4-phenylbutyl)phosphinyl]acetyl]-4-methoxy-L-proline,(2,2-dimethyl-1-oxopropoxy)methyl ester in 5 ml of ethanol and 5 ml of water containing 1.5 ml of 1 N sodium hydroxide is stirred for 16 hours at room temperature. Ethanol is removed in vacuo and water is added. The aqueous layer is washed with ethyl acetate (discard), acidified with 3 ml of 1 N HCl and extracted twice with ethyl acetate. The organic layer is washed with saturated brine, combined, dried (MgSO$_4$) and concentrated in vacuo. The residue is heated in an oil bath at 75° C. under high vacuum for 2 hours. The residue (ca. 150 mg) is dissolved in 0.4 ml of 1 N lithium hydroxide and washed through a column of ion exchange resin (lithium form, 5 ml) with water. The organics containing eluates are combined, Millipore filtered and lyophilized for 16 hours to give 120 mg of product.

EXAMPLE 42

1-[[Ethoxy(4-phenylbutyl)phosphinyl]acetyl]-L-proline,(2,2-dimethyl-1-oxopropoxy)methyl ester A solution of 2.4 g 1-[[ethoxy(4-phenylbutyl)-phosphinyl]acetyl]-L-proline in acetone is treated with 445 mg of potassium carbonate dissolved in a small amount of water. Solvent is removed in vacuo and water is azeotropically removed by addition of toluene and evaporation in vacuo several times. The potassium salt is suspended in fresh acetone and 1.03 g of chloromethylpivalate and 0.5 ml of 25% aqueous sodium iodide is added. The mixture is heated at reflux temperature for 3 hours and allowed to stir at room temperature for 16 hours. The solids are filtered and the filtrate is concentrated in vacuo. The residue (3.3 g) is dissolved in ethyl acetate, washed with 5% sodium bicarbonate, saturated brine, dried ($MgSO_4$), charcoaled and concentrated in vacuo to give 2.65 g of material. Flash chromatography with acetone elution gives 2.4 g of product.

Analysis calc'd for $C_{25}H_{38}NO_7P.1\ H_2O$: C, 58.46; H, 7.85; N, 2.73; P, 6.03; Found: C, 58.30; H, 7.24; N, 2.58; P, 5.98.

EXAMPLE 43

1-[[Hydroxy(4-phenylbutyl)phosphinyl]acetyl]-L-proline,(2,2-dimethyl-1-oxopropoxy)methyl ester, lithium salt An ice cold aqueous dioxane solution of 704 mg of 1-[[hydroxy(4-phenylbutyl)phosphinyl]acetyl]-L-proline,(2,2-dimethyl-1-oxopropoxy)methyl ester is treated with 1.57 ml of 0.96 N lithium hydroxide. Dioxane is removed in vacuo, additional water is added and the solution is lyophilized to give 700 mg of the title compound.

EXAMPLE 44

(cis)-4-(4-Fluorophenoxy)-1-[[ethoxy(4-phenylbutyl)-phosphinyl]acetyl]-L-proline,(2,2-dimethyl-1-oxopropoxy)methyl ester Following the procedure of example 42, but starting with (cis)-1-[[ethoxy(4-phenylbutyl)phosphinyl]acetyl]-4-(4-fluorophenoxy)-L-proline, yields the title compound.

EXAMPLE 45

(cis)-4-(Fluorophenoxy)-1-[[hydroxy(4-phenylbutyl)-phosphinyl]acetyl]-L-proline,(2,2-dimethyl-1-oxopropoxy)methyl ester A solution of (cis)-4-(4-fluorophenoxy)-1-[[ethoxy(4-phenylbutyl)phosphinyl]acetyl]-L-proline,(2,2-dimethyl-1-oxopropoxy)methyl ester (0.24 g) in dichloromethane (2.5 ml), to which bromotrimethylsilane (0.12 g) is added, is stirred at ambient temperature for 16 hours. The mixture is concentrated in vacuo and the residue is treated with water (7 ml). The oil that separates is extracted into ether; the ethereal solution is washed with brine and dried ($MgSO_4$). The solvent is removed in vacuo to give the product as a glass-like solid (0.219 g).

EXAMPLE 46

(cis)-4-(Fluorophenoxy)-1-[[hydroxy(4-phenylbutyl)-phosphinyl]acetyl]-L-proline,(2,2-dimethyl-1-oxopropoxy)methyl ester, lithium salt An aqueous solution of lithium carbonate is added dropwise, with stirring, to a solution of (cis)-4-(fluorophenoxy)-1-[[hydroxy(4-phenylbutyl)phosphinyl]acetyl]-L-proline,(2,2-dimethyl-1-oxopropoxy)methyl ester (0.17 g) in acetone (10 ml); as the stirring solution becomes turbid, the turbidity is clarified by the addition of acetone, so that the final volume of the reaction mixture is 30 ml. A trace of insolubles is removed by filtration. The filtrate is concentrated in vacuo to a volume of 10 ml. After the addition of water (15 ml), the solution is Millipore filtered and lyophilized to give 0.14 g of the title compound.

Analysis calc'd for $C_{29}H_{36}FNO_8P.Li.1.75\ H_2O$: C, 56.63; H, 6.18; N, 2.27; F, 3.09; P, 5.04; Found: C, 56.60; H, 6.15; N, 2.25; F, 2.80; P, 5.10.

EXAMPLE 47

(cis)-4-Cyclohexyl-1-[[ethoxy(4-phenylbutyl)phosphinyl]acetyl]-L-proline (cis)-4-Cyclohexyl-L-proline hydrochloride (3.0 g) in 30 ml acetonitrile is treated with bis(trimethylsilyl)acetonitrile (0.525 g) and stirred until the solid has dissolved. Meanwhile, [(ethoxy)(phenylbutyl)]phosphinyl acetic acid (4.0 g) and carbonyldiimidazole (3.87 g) in 70 ml of acetonitrile are stirred at 0° C. for one hour. The two solutions are combined and stirred for about 16 hours. The mixture is concentrated and the residue is taken up in dichloromethane, washed with 5% potassium bisulfate, and brine, dried ($MgSO_4$) and evaporated to an oil which is chromatographed (20% acetic acid/benzene) to yield 3.36 g of the title compound.

EXAMPLE 48

(cis)-4-Cyclohexyl-1-[[hydroxy(4-phenylbutyl)phosphinyl]acetyl]-L-proline (cis)-4-Cyclohexyl-1-[[ethoxy(4-phenylbutyl)phosphinyl]acetyl]-L-proline, (0.83 g), bis(trimethylsilyl)acetamide (0.47 ml) and bromotrimethylsilane (0.28 ml) are stirred in 20 ml of dichloromethane for about 16 hours. A small amount of water is added and the mixture is evaporated to an oil residue (0.61 g). This material is crystallized from acetone with a recovery of 0.047 g of solid, melting point 175°–176° C.

Anal. Calc'd. for $C_{23}H_{34}NO_5P$, MW 435.50: C, 63.43; H, 7.87; N, 3.22; P, 7.11; Found: C, 62.97; H, 7.93; N, 3.19; P, 7.0.

EXAMPLE 49

(cis)-4-Cyclohexyl-1-[[hydroxy(4-phenylbutyl)phosphinyl]acetyl]-L-proline,(2,2-dimethyl-1-oxopropoxy)-methyl ester (A)

(cis)-1-[(1,1-Dimethylethoxy)carbonyl]-4-cyclohexyl-L-proline,2,2-dimethyl-1-oxopropoxy)methyl ester Following the procedure of example 13A, but substituting (cis)-4-cyclohexyl-L-proline hydrochloride for 1,4-dithio-7-azaspiro[4.4]nonane-8-carboxylic acid, hydrochloride, yields the title compound.

(B) (cis)-4-Cyclohexyl-1-[[hydroxy(4-phenylbutyl)phosphinyl]acetyl]-L-proline,(2,2-dimethyl-1-oxopropoxy)methyl ester A mixture of [hydroxy(4-phenylbutyl)phosphinyl]acetic acid (1.2 g) tetrahydrofuran and carbonyldiimidazole (0179 g) is stirred under argon at 0° C. for 1 hour. (cis)-1-[(1,1-Dimethylethoxy)carbonyl]-4-cyclohexyl-L-proline,(2,2-dimethyl-1-oxopropoxy)methyl ester (2.0 g) is treated with trifluoroacetic acid (approximately 3 ml) and stirred at room temperature for fifteen minutes. The trifluoroacetic acid is removed in vacuo and the residue is taken up in tetrahydrofuran and added dropwise to the above mixture over a thirty minute period at room temperature. After sixteen hours the tetrahydrofuran is stripped and the residue is partitioned between 5% potassium bisulfate and ether. The layers are separated and the organic portion is washed with 5% monobasic sodium phosphate (three times), brine, and dried (MgSO$_4$). The solvent is stripped to yield a solid (2.6 g). Trituration of the crude solid with ether followed by filtration yields crystals (1.8 g), melting point 124°–125° C.

EXAMPLE 50

(cis)-4-Cyclohexyl-1-[[hydroxy(4-phenylbutyl)phosphinyl]acetyl]-L-proline,(2,2-dimethyl-1-oxopropoxy)methyl ester, lithium salt (cis)-4-Cyclohexyl-1-[[hydroxy(4-phenylbutyl)phosphinyl]acetyl]-L-proline, (2,2-dimethyl-1-oxopropoxy)methyl ester (1.21 g) is dissolved in acetone. Lithium carbonate (0.082 g) and water are added to the stirring solution. After three hours some of the acetone is stripped (due to soap-like solution no more acetone can be removed). The remaining solution is lyophilized. The lyophilizate is then redissolved in water, Millipore filtered, and relyophilized. A fluffy solid is obtained (1.1 g).

Anal. Calc'd. for $C_{29}H_{43}NO_7P^-Li^+ \cdot 0.5$ mole of $H_2O$: H, 2.47; C, 61.58; N, 7.84; P, 5.5; Found: H, 2.42; C, 61.43; N, 7.75; P, 5.3.

EXAMPLES 51–55

Following the procedure of Example 42, but substituting the alkylating agent in column I for chloromethylpivalate, yields the compound listed in column II.

| Column I | Column II |
|---|---|
| 51. Br—CH$_2$—O—C(=O)—CH$_3$ | 1-[[ethoxy(4-phenylbutyl)phosphinyl]acetyl]-L-proline,(1-oxoethoxy)methyl ester |
| 52. Cl—CH$_2$—O—C(=O)—O—CH$_2$CH$_3$ | 1-[[ethoxy(4-phenylbutyl)phosphinyl]acetyl]-L-proline,ethoxycarbonyloxymethyl ester |
| 53. Br-phthalide | 1-[[ethoxy(4-phenylbutyl)phosphinyl]acetyl]-L-proline, phthalide ester |
| 54. Cl—CH(CH$_3$)—O—C(=O)—CH$_3$ | 1-[[ethoxy(4-phenylbutyl)phosphinyl]acetyl]-L-proline,1-(1-oxoethoxy)ethyl ester |
| 55. Cl—CH$_2$—O—C(=O)—C$_6$H$_5$ | 1-[[ethoxy(4-phenylbutyl)phosphinyl]acetyl]-L-proline,benzoyloxymethyl ester |

EXAMPLE 56

(cis)-[[Hydroxy(phenylbutyl)phosphinyl]acetyl]-L-proline,(2,2-dimethyl-1-oxopropoxy)methyl ester

(A) (cis)-4-Phenyl-1-phenylmethoxycarbonyl-L-proline

A slurry of (cis)-4-phenyl-L-proline, hydrochloride (3.0 g) in 10 ml of water is cooled in an ice-bath and treated dropwise with a solution of 1.01 g of sodium hydroxide in 10 ml of water. The resulting suspension is treated simultaneously dropwise with benzyl chloroformate (2.28 g) and a solution of 0.5 g of sodium hydroxide in 5 ml of water. Additional water is added to a total volume of about 100 ml. (Vigorous shaking of the flask is needed to insure complete mixing.) After 2 hours, the solids are filtered, washed with water, washed three times with 1:1 ether:acetone, washed with ether and air dried for about 16 hours to give 4.2 g of the sodium salt of the title compound.

The filtrates are combined, concentrated in vacuo and washed with ether. The aqueous layers are acidified with concentrated hydrochloric acid and extracted twice with dichloromethane. The organic layers are washed with saturated brine, dried (MgSO$_4$) and concentrated in vacuo to give 0.4 g of the title compound.

The above 4.2 g of sodium salt is partitioned between dichloromethane (twice) and 25 ml of N hydrochloric acid. The organic layers are washed with saturated brine, dried (MgSO$_4$) and concentrated in vacuo to give 3.17 g of the title compound.

(B) (cis)-4-Phenyl-1-phenylmethoxycarbonyl-L-proline, (2,2-dimethyl-1-oxopropoxy)methyl ester (cis)-4-Phenyl-1-phenylmethoxycarbonyl-L-proline (3.52 g), dissolved in 25 ml of dry dimethylformamide, is treated with 1.61 g of anhydrous potassium fluoride and 2.0 g of chloromethyl pivalate under argon at room temperature for about 16 hours. The reaction mixture is diluted with ethyl acetate and washed with water (three times), saturated sodium bicarbonate and saturated brine. The aqueous layers are backwashed with fresh ethyl acetate. The combined organic layers are dried (MgSO$_4$) and concentrated in vacuo to give 4.86 g of an oil.

(C) (cis)-4-Phenyl-L-proline, (2,2-dimethyl-1-oxopropoxy)methyl ester, p-toluenesulfonic acid salt A solution of 4.86 g of (cis)-4-phenyl-1-(phenylmethoxycarbonyl)-L-proline, (2,2-dimethyl-1-oxopropoxy)methyl ester and 2.31 g of toluene-sulfonic acid monohydrate in 75 ml of ethyl acetate containing 0.5 g of 10% palladium on charcoal is shaken on a Parr hydrogenator at an initial pressure of 35 psi of hydrogen for 45 minutes (final pressure is 26 psi). The precipitated solids are dissolved with dichloromethane and the catalyst is filtered through Celite. The filtrate is concentrated in vacuo and the solid residue is triturated with 100 ml of ethyl acetate, filtered and washed with ether to give 4.14 g of the title compound, melting point 167°–170° C.

(D)

(cis)-1-[[Hydroxy(4-phenylbutyl)phosphinyl]acetyl]-4-phenyl-L-proline, (2,2-dimethyl-1-oxopropoxy)methyl ester A solution of 1.85 g of [hydroxy(4-phenylbutyl)phosphinyl]acetic acid in 50 ml of dry tetrahydrofuran at 0°–5° C. under argon is treated with 1.17 g of carbonyldiimidazole. After stirring at 0°–5° C. for 1 hour, 2.02 ml of triethylamine is added followed by the portionwise addition of (cis)-4-phenyl-L-proline, (2,2-dimethyl-1-oxopropoxy)methyl ester, p-toluene-sulfonic acid salt (4.14 g) over a 20 minute period. An additional 50 ml of tetrahydrofuran is added and the mixture is allowed to stir at room temperature for about 16 hours. Solvent is then removed in vacuo and the residue, dissolved in ethyl acetate, is washed with 10% potassium bisulfate, 5% monobasic sodium phosphate (three times) and saturated brine. The organic layer is dried (MgSO₄) and concentrated in vacuo to give 5 g of crude product. Chromatography of 2.9 g of crude on 70 g of silica gel eluted (i) with 3.5–5% methanol/dichloromethane yields 1.5 g of a mixture (ii) with 7.5% methanol/dichloromethane yields 0.52 g of homogeneous product. Rechromatography of the mixture gives an additional 0.51 g of homogeneous product.

Anal. Calc'd. $C_{29}H_{38}NPO_7 \cdot 1.5\ H_2O$: C, 61.04; H, 7.24; N, 2.45; Found: C, 60.75; H, 6.54; N, 2.53.

EXAMPLE 57

(cis)-1-[[Hydroxy(4-phenylbutyl)phosphinyl]acetyl]-4-phenyl-L-proline

A solution of (cis)-1-[[hydroxy(4-phenylbutyl)phosphinyl]acetyl]-4-phenyl-L-proline, (2,2-dimethyl-1-oxopropoxy)methyl ester (300 mg) is dissolved in 10 ml of 50% aqueous ethanol and treated with 1.5 ml of 1 N sodium hydroxide at room temperature for about 16 hours. The mixture is diluted with 15 ml of water and washed with 4:1 ether/hexane. The organic layer is washed with two fresh 10 ml portions of water. The combined aqueous layer is acidified with 1 N hydrochloric acid and extracted with two 50 ml portions of ethyl acetate. The organic layer is washed with saturated brine, dried (MgSO₄) and concentrated in vacuo to give 150 mg of material. Trituration with ether yields 100 mg of product; melting point softening starts at 80° C., clear at 120° C., after drying in vacuo over phosphorous pentoxide for 5 hours.

What is claimed is:

1. A compound having the formula

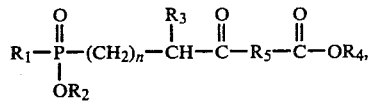

or a non-toxic, physiologically acceptable salt thereof, wherein
   $R_1$ is alkyl, aryl, arylalkyl, cycloalkyl, or cylcoalkylalkyl;
   $R_2$ and $R_4$ each is independently hydrogen, alkyl or arylalkyl;
   $R_3$ is hydrogen or alkyl;
   —$R_5$—COOR$_4$ is

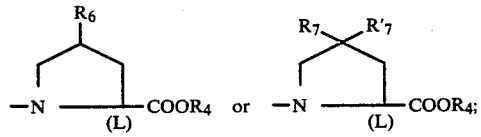

$R_6$ is cycloalkyl or aryl;
   $R_7$ and $R'_7$ together are —S—(CH$_2$)$_2$—S—; and
   n is 0 or 1;
and wherein the term "aryl" refers to phenyl or phenyl substituted with halogen, alkyl, alkoxy, alkylthio, hydroxy, alkanoyl, nitro, amino, dialkylamino, or trifluoromethyl groups; the term "alkyl" refers to groups having 1 to 10 carbon atoms; the term "alkoxy" refers to groups having 1 to 8 carbon atoms; the term "cycloalkyl" refers to groups having 3 to 7 carbon atoms; and the term "alkanoyl" refers to groups having 2 to 9 carbon atoms.

2. A compound in accordance with claim 1 wherein n is 0.

3. A compound in accordance with claim 1 wherein each of R$_2$ and R$_4$ is hydrogen.

4. A compound in accordance with claim 1 wherein —R$_5$—COOR$_4$ is

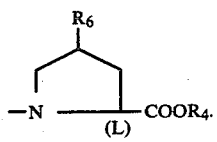

5. A compound in accordance with claim 1 wherein —R$_5$—COOR$_4$ is

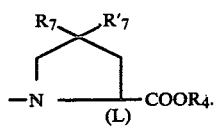

6. The compound in accordance with claim 1, (S)-7-[[hydroxy(4-phenylbutyl)phosphinyl]acetyl]-1,4-dithia-7-azaspiro[4.4]nonane-8-carboxylic acid, or a physiologically acceptable salt thereof.

7. The compound in accordance with claim 1, (cis)-4-cyclohexyl-1-[[hydroxy(4-phenylbutyl)phosphinyl]acetyl]-L-proline, or a physiologically acceptable salt thereof.

8. The compound in accordance with claim 1, (cis)-1-[[hydroxy(4-phenylbutyl)phosphinyl]acetyl]-4-phenyl-L-proline, or a physiologically acceptable salt thereof.

* * * * *